United States Patent
Descamps et al.

(12) 
(10) Patent No.: US 6,620,200 B1
(45) Date of Patent: Sep. 16, 2003

(54) ACETABULAR IMPLANT FOR HIP PROSTHESIS

(75) Inventors: Loys Descamps, 3, Rue de Picardie, Nice (FR), 06000; Guy Derhi, L'Olivade Cedex 231, Roqufort les Pins (FR), 06330; Michel Maestro, 261, Avenue de Fabron, Nice (FR), 06200; Jean-Marc Puch, Le St-Georges 48, Boulevard Pasteur, Nice (FR), 06000; Marcel Remi, 27, Avenue Giacobi, Nice (FR), 06300; Alain Maselli, Flacheres (FR); Sylvain Zanello, Saint Priest (FR)

(73) Assignees: Depuy France, Saint-Priest (FR); Loys Descamps, Nice (FR); Guy Derhi, Roquefort les Pins (FR); Michel Maestro, Nice (FR); Jean-Marc Puch, Nice (FR); Marcel Remi, Nice (FR)

( * ) Notice: Subject to any disclaimer, the term of this patent is extended or adjusted under 35 U.S.C. 154(b) by 0 days.

(21) Appl. No.: 10/089,255
(22) PCT Filed: Sep. 26, 2000
(86) PCT No.: PCT/FR00/02657
§ 371 (c)(1), (2), (4) Date: Jul. 9, 2002
(87) PCT Pub. No.: WO01/24740
PCT Pub. Date: Apr. 12, 2001

(30) Foreign Application Priority Data

Sep. 28, 1999 (FR) .............................................. 99 12085

(51) Int. Cl.$^7$ .................................................. A61F 2/34
(52) U.S. Cl. .................................................. 623/22.32
(58) Field of Search ........................... 623/18.11, 19.11, 623/19.12, 22.11, 22.12, 22.21, 22.22, 22.27, 22.31, 22.32, 22.36, 22.38, 22.39

(56) References Cited

U.S. PATENT DOCUMENTS

| 3,608,096 A | * | 9/1971 | Link ......................... 623/22.39 |
| 5,314,490 A | * | 5/1994 | Wagner et al. ........... 623/22.36 |
| 5,425,778 A | * | 6/1995 | Zichner et al. .......... 623/22.29 |
| 5,702,477 A | * | 12/1997 | Capello et al. ........... 623/22.21 |
| 5,931,870 A | * | 8/1999 | Cuckler et al. ........... 623/22.21 |

FOREIGN PATENT DOCUMENTS

| DE | 197 31 442 | | 2/1999 | |
| FR | 2634372 | * | 1/1990 | .............. 623/22.32 |
| FR | 2 660 546 | | 10/1991 | |
| FR | 2 686 502 | | 7/1993 | |
| FR | 2 710 836 | | 4/1995 | |
| FR | 2 770 769 | | 5/1999 | |

* cited by examiner

*Primary Examiner*—Kevin Shaver
*Assistant Examiner*—Michael B. Priddy
(74) *Attorney, Agent, or Firm*—Young & Thompson

(57) ABSTRACT

An acetubular implant includes a cup for receiving an insert freely articulated in the cup, equipped with iliac expansions (8) and a plugging element; the cup consists of a hemispherical part extended by a cylindrical part whereto are attached the iliac expansions. The cylindrical part extends over substantially a half circumference of an equatorial edge of the hemispherical part and is defined by a plane (R) inclined on the equatorial plane. Part of the outer surface of the cup (2) is covered with a macrostructure (24) defining a set of raised parts with a series of equatorial and meridian grooves of predetermined shape such that the macrostructure is neither too rough nor too smooth.

9 Claims, 7 Drawing Sheets

ACETABULAR IMPLANT FOR HIP PROSTHESIS

CROSS REFERENCE TO RELATED APPLICATION

This is the 35 USC 371 national stage of International Application PCT/FR00/02657 filed on Sep. 26, 2000, which designated the United States of America.

FIELD OF THE INVENTION

The present invention relates to an acetabular implant for a hip prosthesis, of the type comprising a cup which is designed to receive an insert freely articulated in the cup, and which is equipped with iliac extensions and with an obturator element for bone fixation.

This implant is for first intention use and also for revision, that is to say it can be put into place not only the first time, but also if the bone cavity needs to be altered or improved, in other words if the pathology causes bone defects to appear which require grafts of moderate size. In other words, this implant can be used for revision as long as the cotyloid cavity has not been destroyed by more than 50%.

BACKGROUND OF THE INVENTION

French patent 93.12.097 (2,710,836) describes an acetabular implant of this type for a total hip prosthesis in which the cup has a spherical shape, which is the geometry generally used for such implants. However, such a configuration is not particularly well adapted to the anatomy of the acetabular cavity of a hip, the upper wall of which protrudes farther than the lower wall. The result of this is a mechanical stability which leaves something to be desired.

In addition, in the known implants, the iliac tabs generally include a rectilinear part directly attached to the opening edge of the cup. The result of this is a lack of adaptation to the anatomy at this site, in particular to the cotyloid brow, which is likely to affect the proper anchoring of the prosthesis.

A great many known implants have a cup with a smooth surface in contact with the wall of the cotyloid cavity, sometimes equipped with anchoring points, so that their mechanical stability may become compromised in the long term. To remedy these shortcomings, it has been proposed, for example, to perforate the wall of the cotyloid cavity (U.S. Pat. No. 3,740,769, Gierman patent 3,205,526). However, experience has shown that these provisions are not entirely satisfactory.

SUMMARY OF THE INVENTION

The object of the invention is therefore to make available an acetabular implant designed in such a way as to afford it excellent fixation during and after surgery, both in the medium term and in the long term.

According to the invention, the cup consists of a hemispherical part to which the obturator element is fixed and which is continued by a cylindrical part to which the iliac extensions are fixed.

Thus, the cylindrical part, whose width and angular extent are suitably determined, continues the cup in the zone of the iliac extensions, that is to say in the upper part of the cotyloid cavity. This cylindrical part is thus in contact with the bone wall as far as the edge of the acetabular cavity, with which it ensures better contact than a simply hemispherical cup. In other words, the upper part of the implant closely covers the bone wall, which considerably reduces the risk of dislocation in the extreme angular positions of the associated femoral stem and of the insert articulated in the cup.

According to an advantageous embodiment of the invention, the cylindrical part extends over substantially a half-circumference of an equatorial edge of the hemispherical part and is delimited by a plane inclined on the equatorial plane of the hemispherical part, this inclined plane continuing beyond the cylindrical part via a truncated edge of the hemispherical part situated in the same inclined plane.

The advantage of the truncation of the spherical part thus realized in the lower zone of the implant lies in the fact that, in the extreme position of the insert in internal flexion-rotation or in external extension-rotation, it prevents the escape of the insert from the cup by a cam effect. This is because the neck of the femoral stem can no longer come into abutment on the lower opening edge of the cup and thereby risk expulsion of the insert.

In the extreme flexion position, the neck of the femoral stem does not risk coming into abutment against the cylindrical part of the cup, the width of which is suitably chosen for this purpose.

Indeed, this geometry of the acetabular implant greatly reduces the risk of dislocation in the two opposite extreme positions of the insert and of the associated femoral stem, while at the same time promoting excellent angular clearance. Moreover, the geometry of the cup enables it to make maximum provision for the anatomy of the acetabular cavity.

According to another characteristic of the invention, the iliac extensions comprise a rectilinear end attached to the edge of the cup, continued by a curved part whose curvature is adapted to the cotyloid brow of an acetabular cavity, a rectilinear part and then an incurved part continuing said curved part; lastly, a final rectilinear part which is attached to the incurved part and in which a hole is formed for passage of a bone anchoring screw.

Advantageously, the two extreme rectilinear parts delimit between themselves an angle of about 45 degrees preferably.

This geometry allows the iliac extensions to adapt closely to the bone anatomy at this site, near the edge of the acetabular cavity, which edge is itself modeled if necessary.

According to another particular feature of the invention, a macrostructure with raised parts promoting primary anchoring and bone integration is machined on the outer surface of the cup situated substantially between said inclined plane delimiting the opening of the cup and a spherical cap delimiting the bottom of the cup, and this macrostructure and the cap are coated with calcium hydroxyapatite.

This macrostructure, the geometry of which is suitably chosen so as to be neither too smooth nor too rough, permits better primary and long-term anchoring of the cup by means of bone regrowth, thereby giving the implant its long-term stability.

BRIEF DESCRIPTION OF THE DRAWINGS

Other particular features and advantages of the invention will become evident from the following description in which reference is made to the attached drawings which show a nonlimiting illustrative embodiment of the invention.

DETAILED DESCRIPTION OF THE INVENTION

Figure 12:
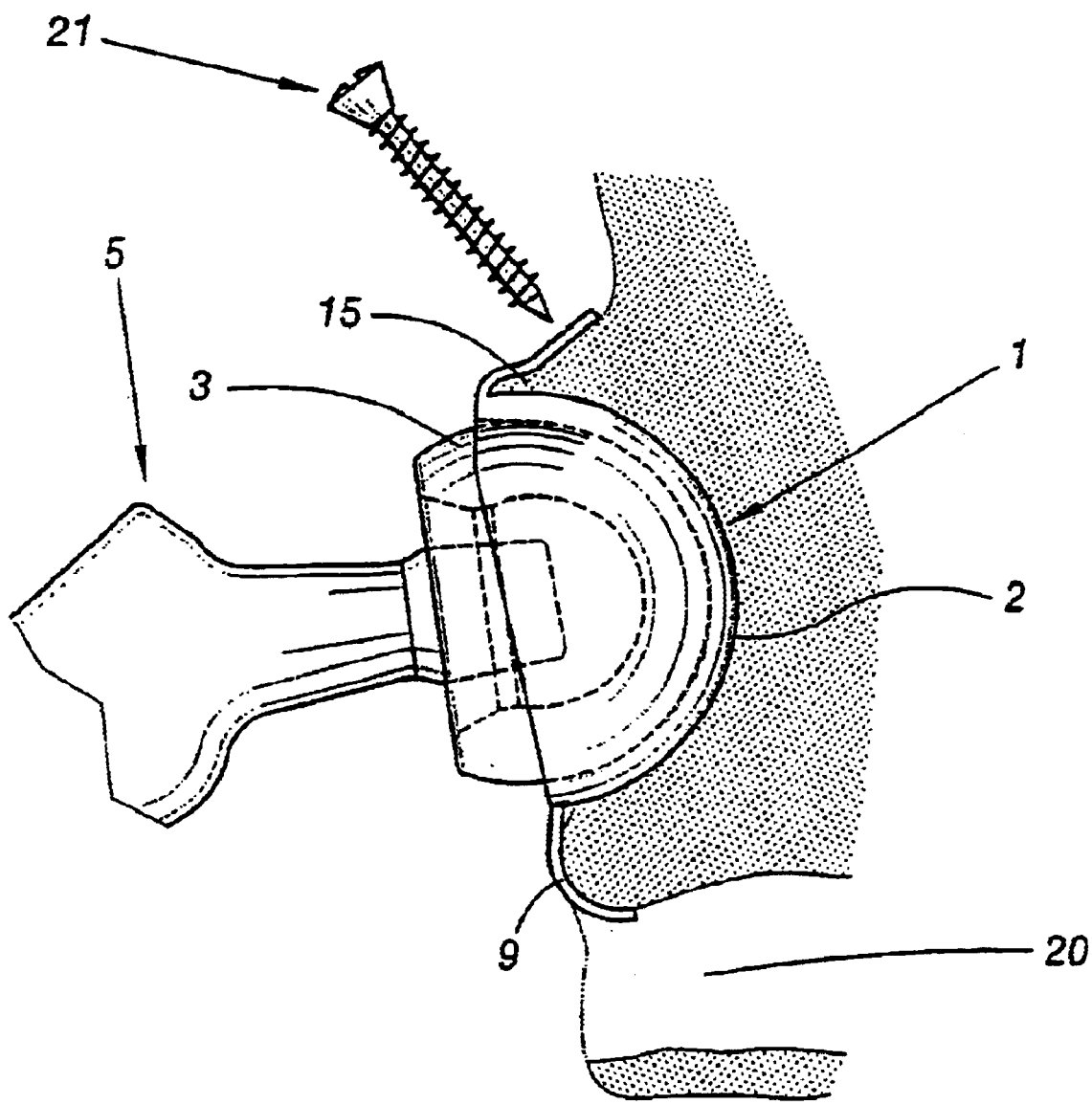
FIG. 12 is an elevation, in a frontal plane, of the implant according to the invention and of the upper end of the associated femoral stem, shown in abduction-extension.
Figure 13:
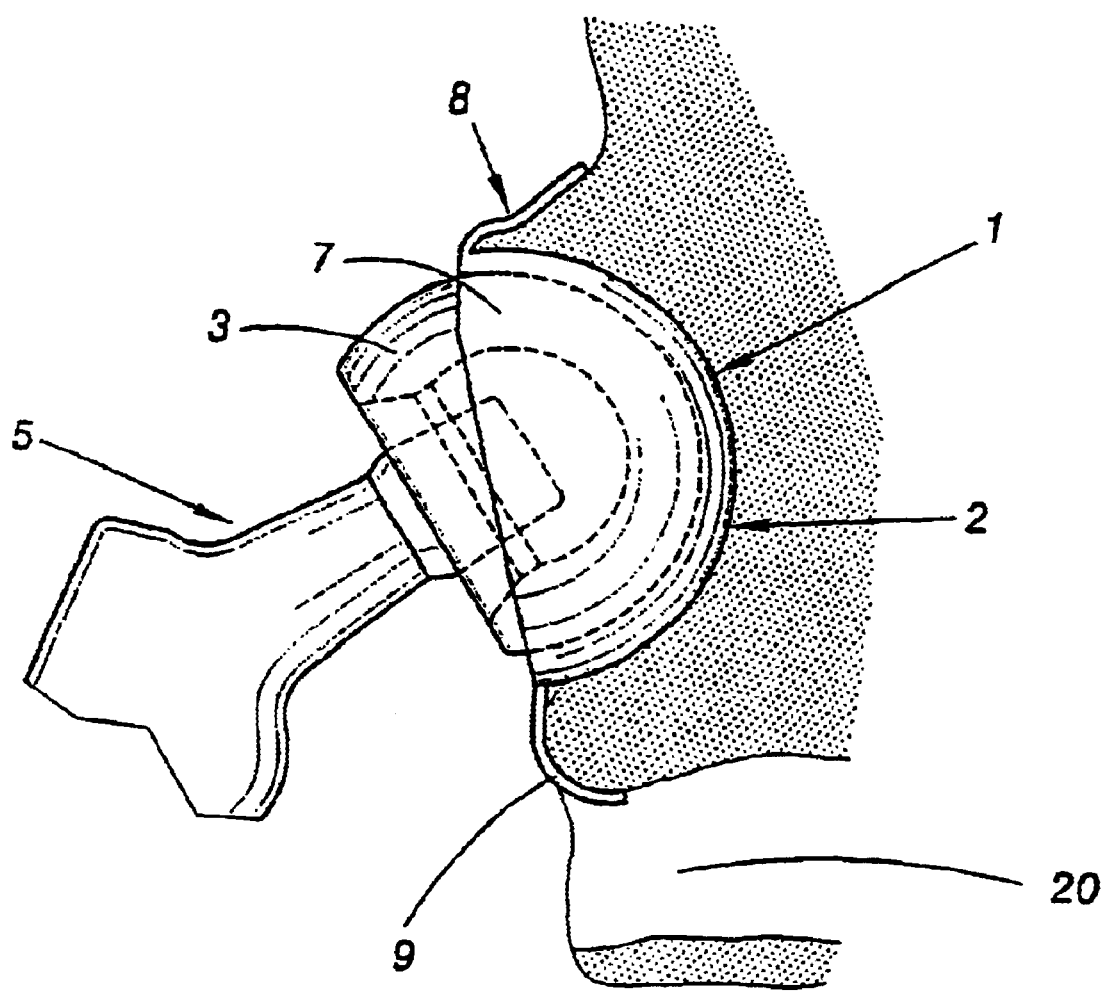
FIG. 13 is an elevation analogous to FIG. 12, showing the extreme position which the femoral stem can adopt in relation to the acetabular implant in adduction-flexion.

The acetabular implant 1 illustrated in the drawings is intended for a total hip prosthesis, of which only the proximal part 5 of the femoral stem has been shown in FIGS. 12 and 13.

The implant 1 comprises a cup 2 designed to receive an insert 3 which is freely articulated in the cup and into which it is possible to introduce a head (FIGS. 12 and 13) attached to the end of the neck of the proximal part 5.

Figure 1:
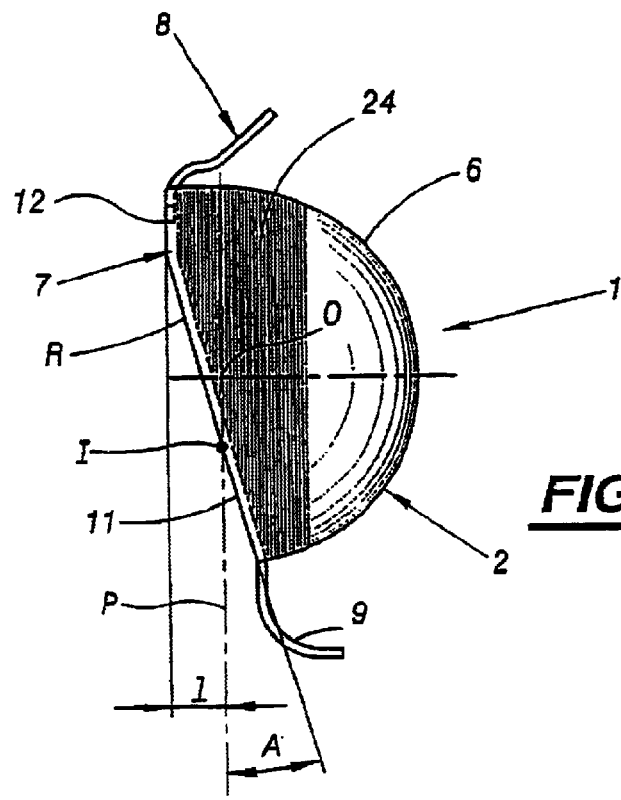
FIG. 1 is a side elevation, substantially to scale, of an embodiment of the acetabular implant according to the invention, viewed in a sagittal plane.
Figure 2:
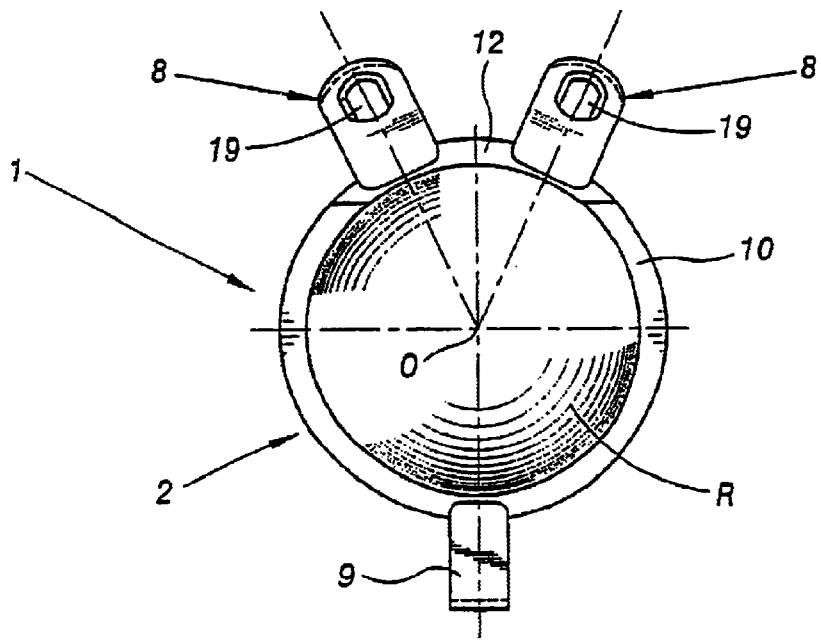
FIG. 2 is an elevation, in a frontal plane, of the implant in FIG. 1.

The cup 2 consists of a hemispherical part 6 delimited by an equatorial plane P (FIG. 1) and continued by a cylindrical part 7 to which two iliac "extensions" 8 are fixed. At the opposite end from these, an obturator element 9 formed by a hook is attached to the lower opening edge of the hemispherical part 6 of the cup 2, at a position diametrically opposite to a point situated at the center of an interval between the extensions 8.

The cylindrical part 7 extends beyond the equatorial plane P, over a part of the circumference of the opening edge of the cup 2, namely over substantially a half-circumference. To be more precise, the cylindrical part 7 in fact extends over an angular sector substantially greater than a half-circumference. It will be seen in FIG. 1 that this part 7 is delimited by a plane R which is inclined on the equatorial plane P and which continues beyond the cylindrical part 7 via a truncated edge 11 of the hemispherical part 6, this truncated edge 11 being situated in the same inclined plane R. A sort of truncation of the hemispherical part 6 is thus formed, extending from the intersection I between the inclined plane R and the equatorial plane P to the lower edge of the cup 2 and to the obturator element 9.

In the radial direction, the cylindrical part 7 has a width 1 appropriate to the anatomy of the cotyloid cavity, and the plane R delimits with the equatorial plane P an angle A of about 15 degrees, the summit of which is the intersection I. The inclined plane R intersects the equatorial plane P between the center O of the hemispherical part 6 and its edge contiguous to the obturator element 9.

The outer edge of the cylindrical part 7 is truncated in such a way as to delimit a bevel 12 which extends parallel to the equatorial plane P and on which the iliac extensions 8 are fixed.

Figure 9:
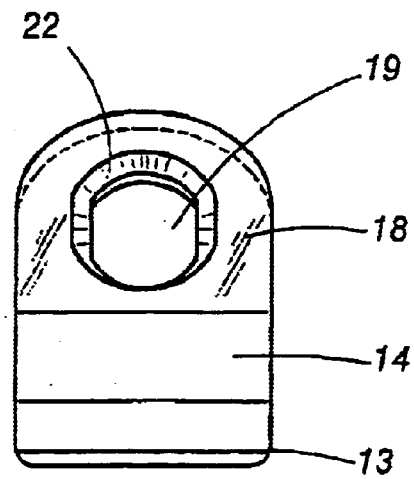
FIG. 9 is an elevation, on an enlarged scale, of an embodiment of an iliac extension attached to an implant according to one of FIGS. 1 to 7.
Figure 10:
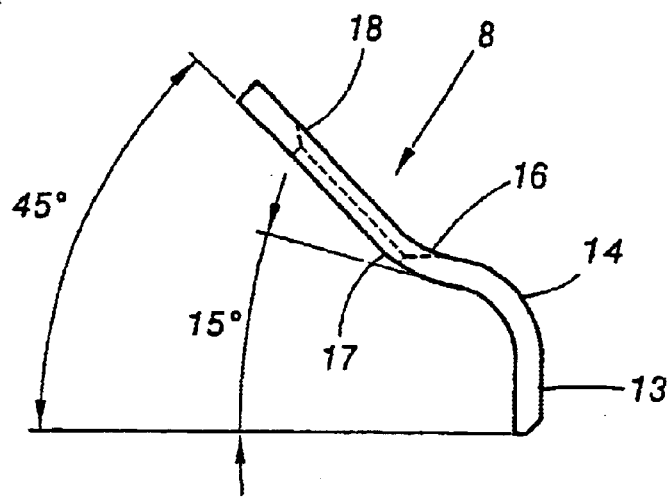
FIG. 10 is a side elevation of the iliac extension in FIG. 9.
Figure 11:
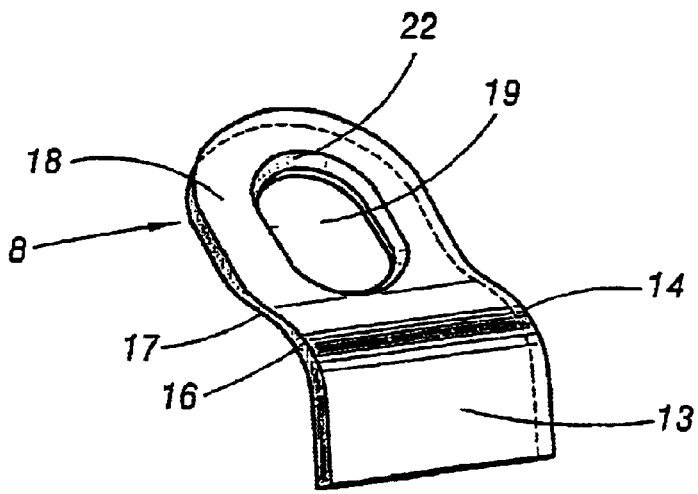
FIG. 11 is a perspective view of the iliac extension in FIGS. 9 and 10.

Each iliac extension 8 can be adapted to the individual bone surface. It comprises a rectilinear end 13 attached to the edge of the cup 2, continued by a curved part 14 whose curvature is adapted to the cotyloid brow 15 of an acetabular cavity (FIG. 12), a rectilinear part 16 and then a second incurved part 17 (FIGS. 9 to 11) continuing said curved part 16; lastly, each extension 8 terminates in a final rectilinear part 18 in which a hole 19, advantageously of oblong shape, is formed for passage of an optional bone anchoring screw 21 (FIG. 12).

The final rectilinear part 18 is advantageously inclined by about 45 degrees on the initial rectilinear part 13 while the intermediate rectilinear part 16 can be inclined by about 15 degrees on the perpendicular to the part 13. The oblong hole 19 is advantageously equipped with a countersink 22 on its circumference, permitting multiple orientation of the anchoring screw 21.

The curvature of the incurved part 14, adapted for the passage of the cotyloid brow, and the angulation of the rectilinear part 18 at 45 degrees in relation to the tab 13 guarantee the proximity between the extensions 8 and the bone surface. Thus, these two particular features ensure excellent respect of the local anatomy by the iliac extensions 8.

A macrostructure 24 with raised parts 28 is machined on a part of the outer surface of the cup 2. This part covered by the miacrostructure 24 is delimited substantially by the opening edge 10 of the cup 2 and a spherical cap 25 forming the bottom of the cup 2. This macrostructure 24 and the cap 25 are coated with a layer of calcium hydroxyapatite which contributes, along with the macrostructure 24, to bone regrowth and bone integration.

The macrostructure 24 is separated from the free edge 10 of the cup 2 by a smooth band 26 of small width. The macrostructure 24 delimits a set of equatorial grooves 26 situated in equatorial planes parallel to the plane P, and a set of meridian grooves 27 perpendicular to the equatorial grooves 26. This assembly of grooves 26 and 27 thus forms a sort of gridiron delimiting, at the intersections between the grooves 26 and 27 whose cross sections have a V-shaped profile (FIGS. 3 to 8), a series of raised parts 28 each having a rectangular base.

The flanks 26a of the equatorial grooves 26 can be inclined advantageously Abut without implying any limitation) by an angle B of about 30 degrees on a median plane M passing through the base of each groove 26, whose angle of opening is thus 60 degrees and whose depth can be about 1 mm, for example.

Figure 7:
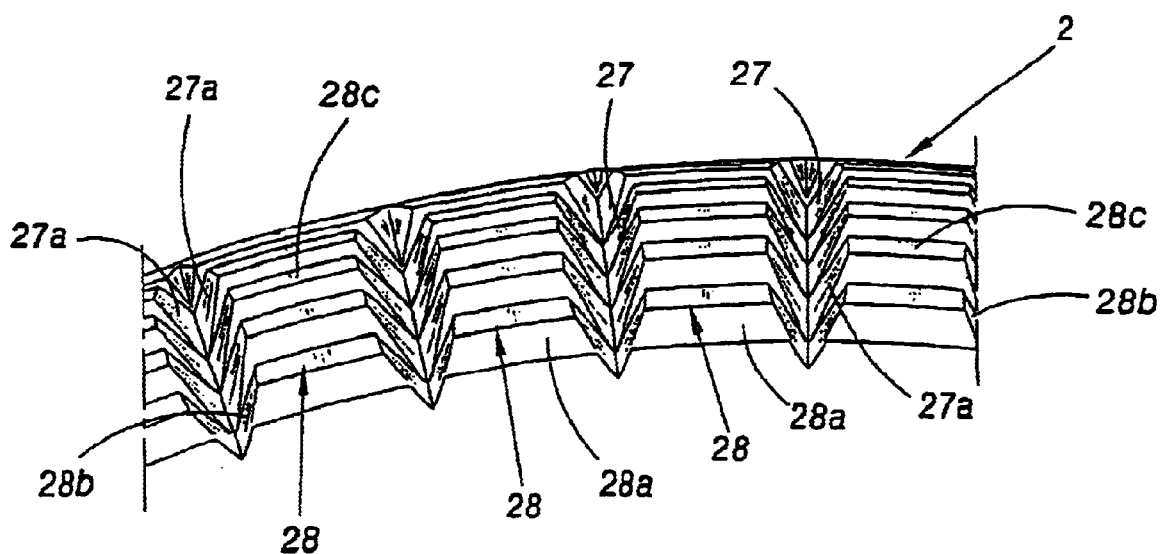
FIG. 7 is a perspective view, on an enlarged scale, of a detail of the outer surface, with macrostructure, of the implant in FIGS. 3 to 6.
Figure 8:
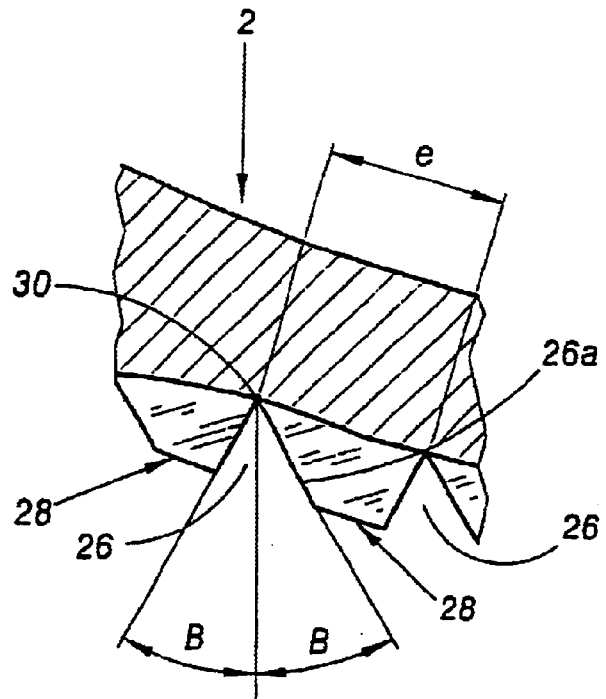
FIG. 8 is a partial sectional view, on an enlarged scale, of equatorial grooves visible in FIGS. 3 to 6.

The same applies to the flanks 27a of the meridian grooves 27 (FIG. 7). Moreover, and again by way of a nonlimiting numerical example, the ridges forming the bottom of the equatorial grooves 26 can be spaced apart by an interval e of about 2 mm (FIGS. 6 and 8), the number of these equatorial grooves 26 varying with the size of the cup 2.

Finally, the meridian grooves 27 are spaced apart in pairs by an angle of advantageously about 6 degrees (FIG. 7) so that their total number on the circumference of the cup 2 is 60. This total number is constant irrespective of the size of the cup.

Figure 3:
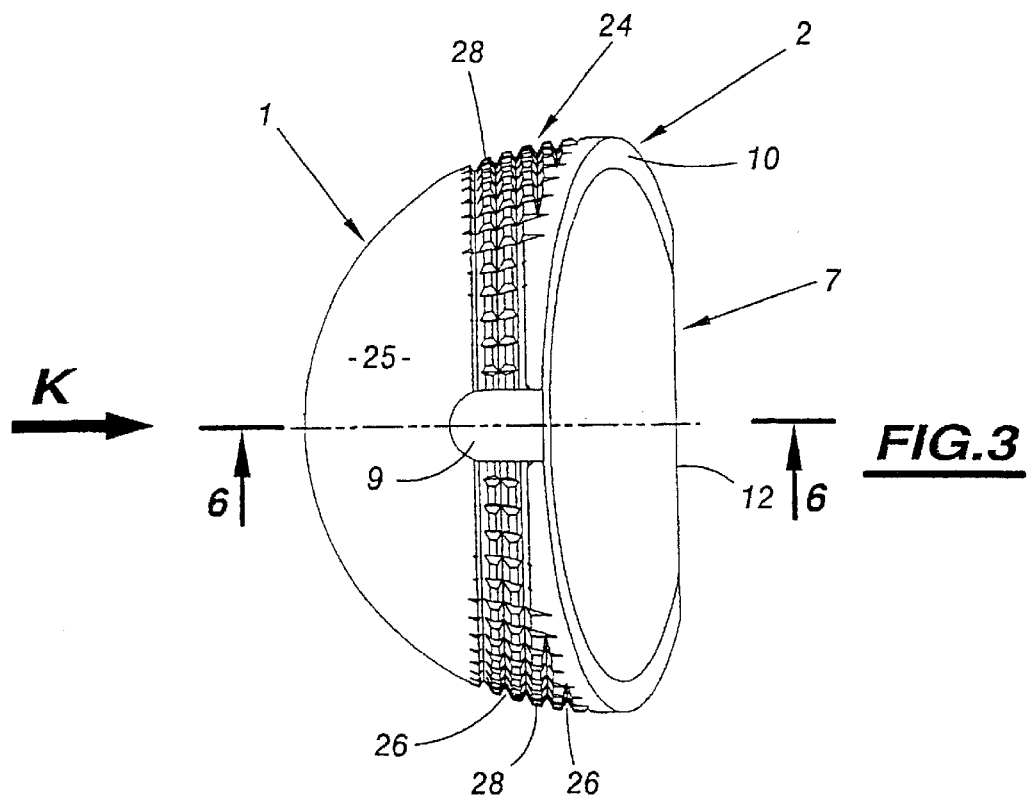
FIG. 3 is an elevation, on an enlarged scale compared to FIGS. 1 and 2, of an industrial embodiment of the implant according to the invention.
Figure 4:
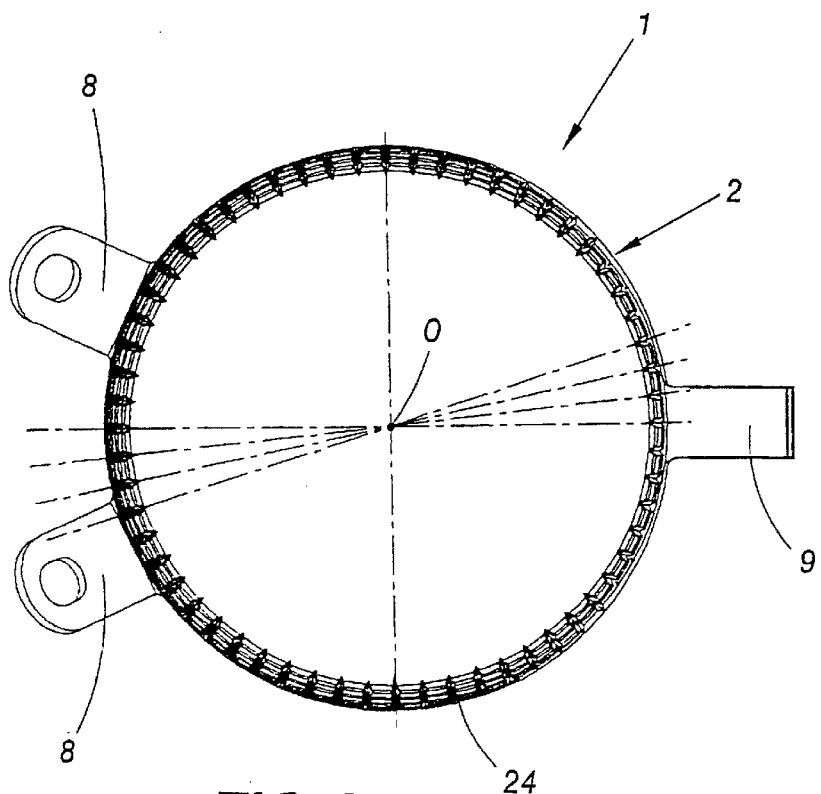
FIG. 4 is an elevation along the arrow K in FIG. 3.
Figure 5:
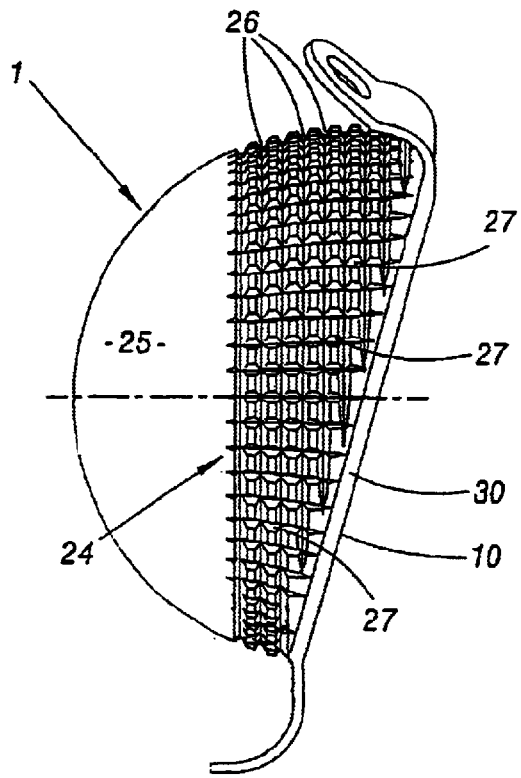
FIG. 5 is an elevation of the acetabular implant in the direction of the arrow K in FIG. 3.
Figure 6:
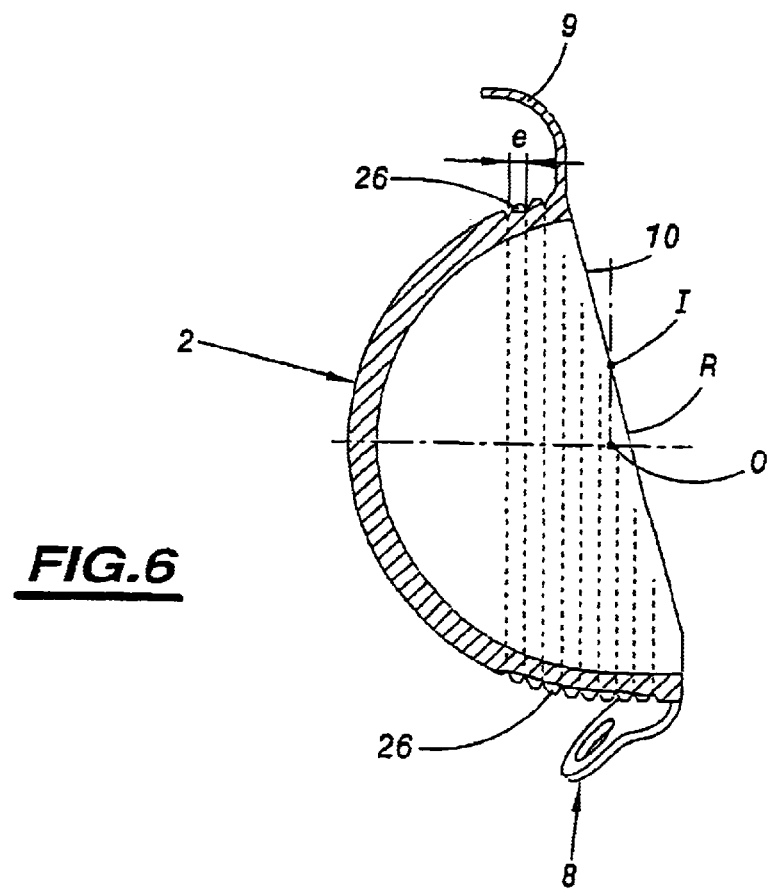
FIG. 6 is a sectional view along 6—6 in FIG. 3.

It will be seen from FIGS. 3 and 7 that each of the raised parts 28 has transverse and longitudinal profiles whose transverse flanks 28a delimit equatorial grooves 26, while their longitudinal flanks 28b delimit meridian grooves 27. All these flanks are joined to a flat face 28c.

The cup 2, which is not cemented, can be made, for example, of stainless steel of standard ISO 53 32-1, covered with calcium hydroxyapatite (CHA).

The acetabular implant 1 which has just been described is put into place in the manner shown in FIG. 12: its dimensions are chosen so that the diameter of the cup 2 is slightly greater than the diameter of the natural cotyloid cavity in which it is to be implanted by means of a press fit, that is to say by impaction. At the same time, the iliac extensions 8 take up their position straddling the cotyloid brow 15, while the obturator element 9 is introduced into the obturator foramen 20. If necessary, the screws 21 are implanted through the holes 19 in the appropriate orientation to find the best bone anchoring, which screws 21 can be of the spongy bone type or of the cortical bone type.

The immediate stability of the cup 2, during and after surgery, is ensured by the combination of the following elements:

the press-fit impaction of the implant 1 in the natural cotyloid cavity, the presence of the macrostructure 24 coated with hydroxyapatite, the (optional) screwing of the iliac extensions with the screws 21, the positioning and securing of the cup 2 by the obturator element 9.

The stability of the implant in the medium and long term is obtained by the osseoconduction induced by the calcium hydroxyapatite coating, by the osseointegration at the heart of the macrostructure 24 and, possibly, by the action of the iliac extensions 8 and of the obturator element 9.

Thus, all these elements guarantee excellent primary and secondary fixation of the implant 1 and, consequently, an optimum lifetime.

The iliac extensions 8 adaptable to the bone, whose surface they match, and the obturator element 9 permit gripping of the ischiopubic branch.

The presence of the smooth band 30 avoids indentation of the equatorial plane P by the edge of the macrostructure 24. Moreover, the numerical values indicated above, although nonlimiting, have proven, in tests, to provide the most advantageous results in terms of improving the efficacy of the primary and long-term secondary fixation of the implant. Thus, the fact that the total number of meridian grooves 28 is limited to 60 irrespective of the size of the acetabular implant means that it is possible, for large sizes, to form large gridirons which have large raised parts 28 and which promote attachment to the bone wall. The macrostructure 24 is advantageously machined on the cup 2, and not added to it, as this has proven more effective in terms of osseointegration.

Moreover, it has been found that there is no point in arranging a macrostructure 24 on the spherical cap 25 which comes into contact with the bottom of the natural cotyloid cavity. This is because the stresses acting at this level are low, whereas they are at their greatest in the upper zone of the cotyloid cavity, the forces exerted diminishing in the posterior and anterior zones of the cavity.

In summary, the geometry of the cup 2, hemispherical and surmounted by a cylindrical part 7, with truncation at 15 degrees through the plane R, permits excellent angular clearance as far as the limit positions and avoids the risks of dislocation in these extreme positions, while at the same time also respecting the anatomy of the acetabular cavity to the greatest possible extent.

The geometry of the iliac extensions 8 ensures their optimal contact with the bone surface, in particular by virtue of the bend on these extensions at the level of their incurved part 14.

The combination of the macrostructure 24, whose geometry is well defined, as has been explained above, and of a coating of calcium hydroxyapatite ensures, on the one hand, good penetration of the bone trabeculae within the macrostructure 24, that is to say promotes good osseointegration, and, on the other hand, guarantees the stability of the acetabular implant over the course of time.

The invention is not limited to the described embodiments and can include numerous alternatives. Thus, the dimensions and the geometry of the raised parts 28 defined by the macrostructure 24 could differ substantially from the example described, likewise the inclination of, for example, the plane R on the equatorial plane P.

What is claimed is:

1. An acetabular implant (1) for a hip prosthesis, comprising a cup (2) which is designed to receive an insert (3) freely articulated in the cup, and which is equipped with iliac extensions (8) and with an obturator element (9) for bone anchoring, which cup comprises a hemispherical part (6) to which the obturator element (9) is fixed and which is continued by a cylindrical part (7) to which the iliac extensions (8) are fixed, wherein said cylindrical part (7) extends over substantially a half-circumference of an equatorial edge of the hemispherical part (6) and is delimited by a plane R inclined on the equatorial plane (P) of the hemispherical part (6), the inclined plane continuing beyond the cylindrical part (7) via a truncated edge (11) of the hemispherical part (6) situated in the same inclined plane (R).

2. The implant as claimed in claim 1, wherein said inclined plane (R) delimits, with the equatorial plane (P) of the cup (2), an angle (A) of about 15 degrees, which intersects the equatorial plane between the center (O) of the hemispherical part (6) and its edge contiguous to the obturator element (9), the cylindrical part (7) having a width (1) appropriate to this purpose.

3. The implant as claimed in claim 1, wherein the iliac extensions (8) comprise a rectilinear end (13) attached to the edge of the cup (2), continued by a curved part (14) whose curvature is adapted to the cotyloid brow (15) of an acetabular cavity, a rectilinear part (16) and then an incurved part (17) continuing said curved part, and lastly a final rectilinear part (18) which is attached to the incurved part and in which a hole (19) is formed for passage of a bone anchoring screw (21).

4. The implant as claimed in claim 3, wherein the final rectilinear part (18) is inclined by about 45 degrees on said rectilinear end (13), the hole (19) is oblong and comprises a countersink (22) permitting multiple orientation of the bone anchoring screw (21).

5. The implant as claimed in claim 1, wherein a macrostructure (24) with raised parts (28) promoting bone integration is machined on the outer surface of the cup (2) situated substantially between said inclined plane (R) delimiting the opening of the cup (2) and a spherical cap (25) delimiting the bottom of the cup, and the macrostructure and the spherical cap are coated with calcium hydroxyapatite.

6. The implant as claimed in claim 5, wherein a smooth band (30) is reserved between an opening edge (10) of the cup (2) and the start of the macrostructure (24) with raised parts (28).

7. The implant as claimed in claim 6, wherein the macrostructure (24) delimits a set of equatorial grooves (26), situated in parallel equatorial planes, and a set of meridian grooves (27) perpendicular to the equatorial grooves, and the different equatorial and meridian grooves have a V-shaped cross section whose flanks (26a) are inclined by about 30 degrees on a median plane (M) passing through the bottom of the groove (26, 27), while the depth of these equatorial and meridian grooves is about 1 mm.

8. The implant as claimed in claim 7, wherein the bottom of the equatorial grooves forms ridges (26), which are spaced apart by about 2 mm and the number of these grooves varies with the size of the cup (2).

9. The implant as claimed in claim 7, wherein the meridian grooves (27) are spaced apart in pairs by an angle of about 6 degrees so that their total number on the circumference of the cup (2) is 60, said total number being constant irrespective of the size of the cup.

* * * * *